United States Patent [19]

Fairchild et al.

[11] Patent Number: 5,032,112

[45] Date of Patent: Jul. 16, 1991

[54] DUAL SOURCE INTRAVENOUS ADMINISTRATION SET HAVING AN INTRAVENOUS PUMP

[75] Inventors: Michael S. Fairchild, Hoffman Estates; Joseph B. Matthews, Grayslake; Roberta Scola, Elk Grove; Mark Senninger, Chicago, all of Ill.

[73] Assignee: Baxter International Inc., Deerfield, Ill.

[21] Appl. No.: 440,528

[22] Filed: Nov. 22, 1989

[51] Int. Cl.⁵ ............................................. A61M 5/14
[52] U.S. Cl. ...................................... 604/80; 604/123; 604/151
[58] Field of Search ................ 604/80, 81, 151–153, 604/123

[56] References Cited

U.S. PATENT DOCUMENTS

| | | |
|---|---|---|
| 1,796,126 | 3/1931 | Smith . |
| 3,097,366 | 7/1963 | Winchell .......................... 3/1 |
| 3,559,644 | 2/1971 | Shaw . |
| 3,620,650 | 11/1971 | Shaw .......................... 417/417 |
| 3,656,873 | 4/1972 | Schiff .......................... 417/395 |
| 3,868,973 | 3/1975 | Bierman et al. ................. 138/43 |
| 4,094,318 | 6/1978 | Burke et al. . |
| 4,105,028 | 8/1978 | Sadlier et al. . |
| 4,105,029 | 8/1978 | Virag . |
| 4,121,584 | 10/1978 | Turner et al. . |
| 4,200,095 | 4/1980 | Reti . |
| 4,265,240 | 5/1981 | Jenkins . |
| 4,336,800 | 6/1982 | Giovanni Pastrone . |
| 4,392,791 | 7/1983 | Mandroian ..................... 417/379 |
| 4,451,255 | 5/1984 | Bujan et al. ................... 604/157 |
| 4,563,170 | 7/1983 | Aigner .............................. 604/5 |
| 4,648,877 | 3/1987 | Lundback .......................... 623/3 |

OTHER PUBLICATIONS

The Lancel, "A Bood Pump Which Minimises Hemolysis", E. Rotellar, Jan. 25, 1958, p. 197.

Primary Examiner—Stephen C. Pellegrino
Assistant Examiner—Ralph A. Lewis
Attorney, Agent, or Firm—Paul E. Schaafsma; Bradford R. L. Price; Paul C. Flattery

[57] ABSTRACT

The present invention provides an intravenous administration set 10 having a primary container 22 and a secondary container 24, each containing fluid, and a pump 20. The primary container 22 and secondary container 24 are joined into a single flow path by a Y-site 50. A check valve 42 is provided between the primary container 22 and the Y-site 50. A fluid capacitor 60 is provided on the single flow path between the Y-site 50 and the pump 20 to repenish displaced fluid in the pump 20.

14 Claims, 2 Drawing Sheets

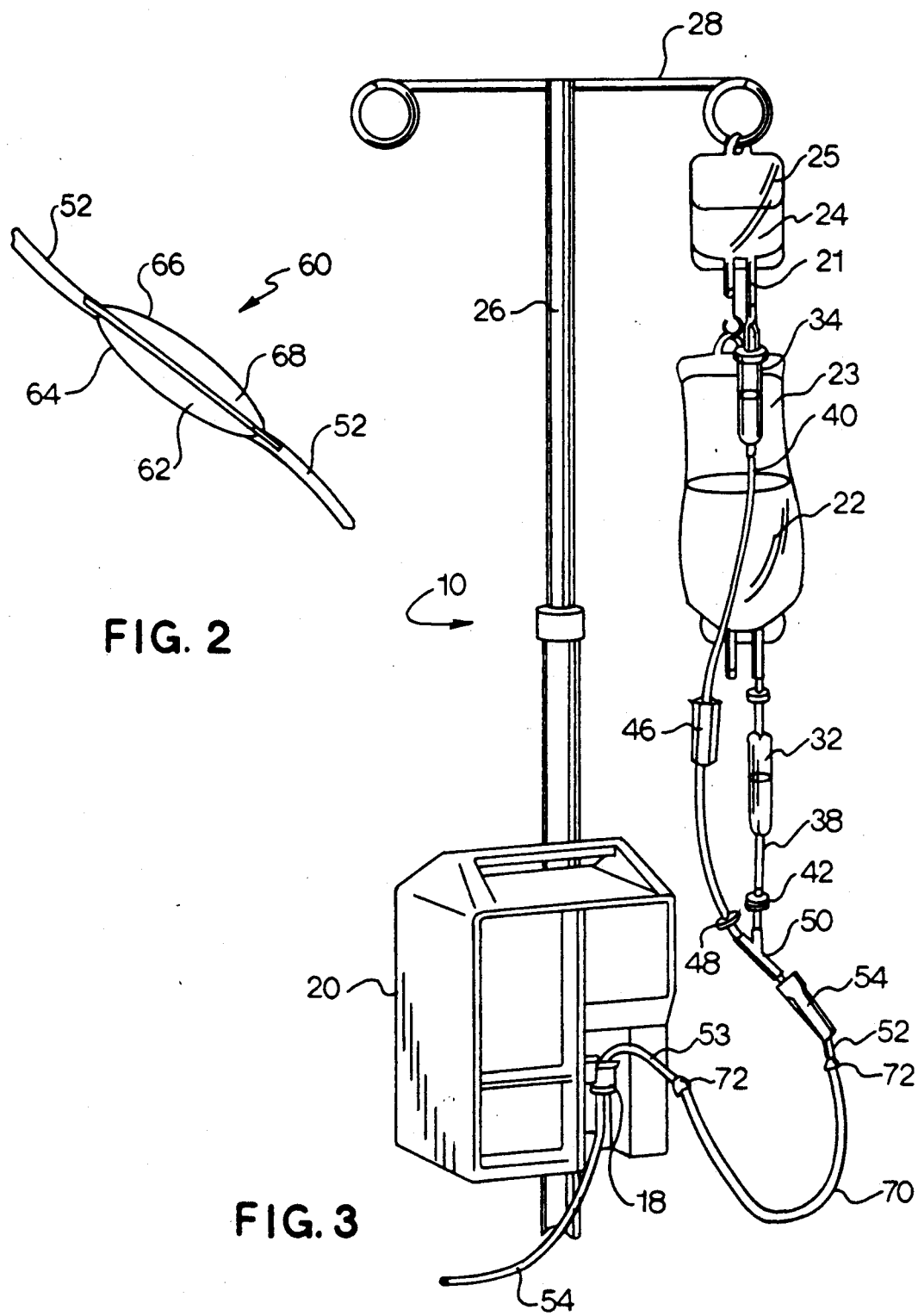

DUAL SOURCE INTRAVENOUS ADMINISTRATION SET HAVING AN INTRAVENOUS PUMP

FIELD OF THE INVENTION

The present invention relates in general to intravenous administration sets and in particular to an intravenous administration set which is especially adapted for use with an intravenous administration pump when fluid is being supplied to a patient from two sources.

BACKGROUND OF THE INVENTION

Administration of intravenous fluids to a patient is well known in the art. Typically a solution such as saline, glucose or electrolyte in a glass or flexible container is fed to a patient's venous access site via a length of flexible plastic tubing, called an administration set. The rate of flow of the fluid is controlled by a roller clamp which is adjusted to restrict the flow lumen of the set until the desired flow rate is obtained.

In some cases an intravenous administration set up includes a second container of fluid, usually containing a medication such as an antibiotic. In that instance the administration set includes three branches connected by a Y-site. One branch is connected to the first container, one branch is connected to the second container, and the third branch is connected to the patient access site. When two containers are used, one of the containers is hung at a higher elevation than the other. The higher head pressure that results from the higher elevation causes the higher container to empty before the lower one. A check valve is provided in the Y-site branch leading to the lower container so that fluid will flow from the higher container to the patient, and not to the lower container.

This two container arrangement is typically used when a patient is scheduled to receive an intermittently administered medication. In that instance the line from the upper container to the Y-site is clamped off until the time when the medication is to be administered. Until then, fluid from the lower container is continually supplied to the patient at the desired rate. When the medication is to be administered the clamp to the upper container is opened. The greater head pressure in the upper container causes the fluid to flow from that container, and automatically cuts off the flow from the lower container. When the upper container is emptied, flow from the lower container will automatically resume to the patient.

Flow from the two containers to the patient may also be regulated by means other than a roller clamp. It is becoming more and more common to use an electronically controlled pump.

If a single pump is positioned between the Y-site and the patient access site in a two container set up, its use does not affect the preferential flow from the higher container. The pump will control the rate of flow to the patient regardless of which source the fluid is coming from.

One type of pump that is used for intravenous fluid administration has a pump cassette which is positioned in the fluid flow path between the patient and the fluid source. The cassette has a variable volume pumping chamber connected via tubing at its inlet side to tubing that is connected to the fluid source, and at its outlet side to tubing that is connected to the patient's access site.

In operation the pump cassette is positioned in a pump which has an operating mechanism to force fluid from the source to the patient by expanding and contracting the volume of the pumping chamber. Expansion draws fluid into the chamber from the fluid source, and contraction forces the fluid from the chamber to the patient. An example of such a pump and cassette is shown in U.S. Patent Application No. 07/411,789 filed Sept. 25, 1989 and assigned to the assignee of the present invention, the disclosure of which is incorporated herein.

A characteristic of intravenous pumps of this type is that when the pump chamber is being filled, the expansion of its volume causes a pressure drop to occur upstream of the chamber. This drop in pressure is not a problem when only a single fluid source is employed. However, when there are two fluid sources with one at a higher elevation than the other, the pressure drop can have the effect of lowering the pressure at the check valve to a value that is lower than the pressure upstream of the valve. This opens the check valve and permits fluid to flow from the primary (lower) container.

In order to overcome this problem it has been proposed in the prior art to isolate the effect of the pressure drop by interposing a restriction in the flow path between the pump and the fluid sources, or by using an air chamber in the same location. Both of these have disadvantages. The restriction also limits the flow rate from the fluid source to the pumping chamber and thus affects speed and accuracy of the pump. The air chamber is undesirable because it is position sensitive and suffers from the drawbacks of introducing air into an intravenous administration line.

SUMMARY OF THE INVENTION

The present invention provides an intravenous administration set for use when fluid is pumped from more than one source, such as in a dual container arrangement previously described. The set is equipped with an expandable chamber, called a fluid capacitor, which is positioned between the pumping chamber and the fluid sources Beginning when the set is primed for operation, the capacitor is in a normally filled condition, as is the rest of the fluid line from the drip chamber that is connected to the container, to the pumping chamber and from the pumping chamber to the patient. The capacitor preferably has a volume that is greater than the volume of the pumping chamber. When the pump is operated to draw fluid into the pumping chamber, the pressure drop upstream of the chamber will cause fluid to be drawn from the capacitor, causing its walls to contract and isolating the effect of the pressure drop from the upstream fluid containers. If at the time fluid is being drawn from the upper container, the effect of the capacitor will be to prevent fluid from being drawn from the lower container.

BRIEF DESCRIPTION OF THE DRAWINGS

FIG. 2 is an elevational side view of a fluid capacitor in accord with the principles of the present invention; and FIG. 3 is a perspective view of an alternative embodiment of a fluid damping device in accord with the principles of the present invention.

DETAILED DESCRIPTION OF A PREFERRED EMBODIMENT

Figure 1:
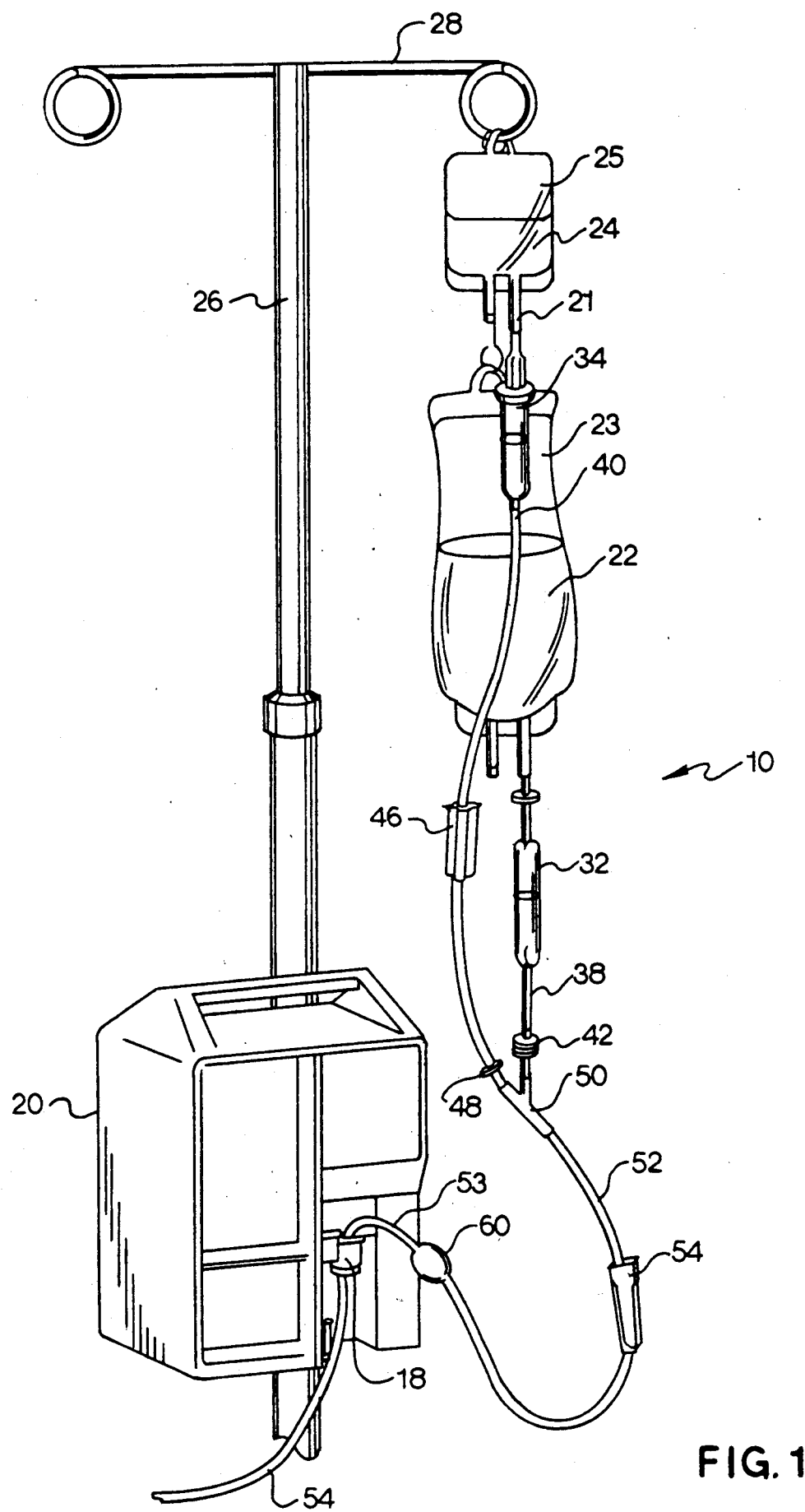
FIG. 1 is a perspective view of an intravenous pump set utilizing a primary and a secondary fluid source.

FIG. 1 is an illustration of an intravenous administration set up using a pump and two sources of intravenous fluid such as flexible containers. Pump 20, which is provided with a pump operating mechanism and operating electronics (not shown), is mounted on an I.V. stand 28 which also serves as a support for the intravenous fluid containers 22 and 25. Container 22, which typically contains a fluid such as saline that is continually administered, is suspended from stand 28 at an elevation that is lower than that of container 25. Container 25 is usually smaller than container 22, and can be used to hold an intermittently administered medication, such as an antibiotic or another beneficial agent.

An administration set 10 provides a flow path from containers 22 and 25 to the patient via pump 20. Set 10 is equipped with a Y-site 50 with first and second branches that lead to containers 22 and 25, and a third branch, which leads to the patient.

The branch of Y-site 50 that leads to upper container 24 has attached to it a tubing segment 40. Segment 40 at its opposite end is attached to a drip chamber 34 that in turn is attached via a spike (not shown) to an outlet port 21 of container 24. A clamping means such as a roller clamp 46 is positioned on segment 40 at a point between Y-site 50 and container 24. A connector site 48 may be provided to join segment 40 to Y-site 50.

In similar fashion, the branch that leads from Y-site 50 to lower container 22 has a tubing segment 38, and a combined drip chamber and spike 32. In addition this branch is provided with a check valve 42 that is closed when pressure in the branch leading to upper container 24 is greater than in the branch leading to lower container 22; i.e., when fluid is flowing from upper container 24 to the patient.

The branch of set 10 leading from Y-site 50 to the patient has a first tubing segment 52, a roller clamp 54, a fluid capacitor 60, a second tubing segment 53, a pump cassette 18, and a third tubing segment 54. Segment 54 has connected at its end distal from cassette 18 means for connecting set 10 to a vein access device, such as a catheter or needle (not shown).

Although shown as a single unit, it should be understood that set 10 may be supplied in several parts which are assembled at the patient site. For example, tubing segment 40 may be preconnected to Y-site 50, or may be provided, with drip chamber 34, roller clamp 46 and connector 48 as a separate set with tubing segment 38, drip chamber 32, filter 42, Y-site 50, tubing segment 52, fluid capacitor 60, tubing segment 13, cassette 18, and tubing segment 54 provided as a set. Similarly, the entire segment from Y-site 50 to the vein access device may be preattached, or segment 54 and pump cassette 18 may be provided separately.

Referring now to FIG. 2, an elevational side view of a fluid capacitor 60 in accordance with the principles of the present invention is seen. Fluid capacitor 60 has an enlarged fluid chamber 62. This enlarged fluid chamber 62 is constructed of two sheets 64,66 of flexible material such as preferably vinyl. While the present invention contemplates various shapes for the flexible material, in the preferred embodiment, the sheets 64,66 are round.

The two sheets 64,66 of fluid capacitor 60 are joined together at the outer periphery 68 of each by, for example, radio frequency or heat sealing while the upstream and downstream tubing segments 52, 53 are radio frequency or heat sealed into the outer periphery 68, thus establishing fluid communication through the fluid capacitor 60.

Fluid capacitor 60 has a fluid volume that, when capacitor 60 is expanded is sufficient to dampen the sudden pressure drop which results from the intake stroke of pump chamber 18. Preferably, the volume of fluid capacitor 60 is greater than the maximum volume of pump chamber 18. This assures that sufficient fluid will be available to fill pumping chamber 18 without transmitting the pressure drop upstream of capacitor 60.

An alternative embodiment of the present invention is seen in FIG. 3, in which like elements are designated by the same reference numerals. In this embodiment, a length of expandable diameter tubing 70 is provided upstream of pump chamber 18 and downstream of Y-site 50. Expandable diameter tubing 70 is attached to standard tubing 52 by a pair of connectors 72. Expandable diameter tubing 70 is preferably a non-PVC material such as silicone as PVC tubing exhibits poor diameter expandability.

The required length of expandable diameter tubing 70 is dependent on a number of factors, including the degree of the expansion of the diameter of tubing 70 and the inner diameter of tubing 70. Once again, the volume of the fluid subject to the expansion of the tubing must be sufficient to dampen the sudden pressure drop which results from pump chamber 18. Preferably, the volume of the fluid subject to the expansion of tubing 70 is equal or greater than the volume of pump chamber 18.

Referring again to FIG. 1, the operation of the present invention will be described. The administrative set 10 is assembled and primed as known in the art. During the priming operation, fluid capacitor 18 fills with fluid from the priming source. The intravenous pump 20 is set at a desired flow rate. While roller clamp 46 is closed, pump 20 will draw fluid from container 22 through, respectively, fluid capacitor 60, Y-site 50, check valve 42, and drip chamber and spike 32.

When the delivery of fluid from container 24 is desired, such as for delivery of beneficial agent, roller clamp 46 is opened. Under normal operating conditions, the height of container 24 results in the pressure of the fluid supplied at Y-site 50 from container 24 being greater than the pressure of the fluid from container 22. This results in fluid flow from container 24 only.

With the pump 20 in operation, during each pumping cycle the volume of pump chamber 18 is decreased to impart fluid propulsion on the fluid. After each pump cycle, a sudden drop in pressure is experienced upstream of pump chamber 18 as fluid rushes into pump chamber 18. If this reduced pressure or pressure drop reaches Y-site 50 and check valve 42, the pressure downstream of check valve 42 could be less than the pressure upstream from check valve 42, which would result in fluid being drawn from container 22.

As a result of the flexibility of sheets 64,66 of fluid capacitor 60, fluid stored in fluid capacitor 60 is drawn into pump chamber 18 to dampen the sudden pressure drop. Additionally, the amount of fluid in fluid capacitor 60 is sufficient to fill pump chamber 18. Accordingly, the pressure drop does not reach check valve 42 and fluid is continuously drawn from container 24.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An intravenous administration set comprising:
   means for connecting said set to a source of intravenous fluid;
   a drip chamber connected to said connecting means;
   a first tubing segment connected at one end to said drip chamber and at its other end to a first branch of a Y-site;
   valve means associated with said first tubing segment and said Y-site for preventing flow through said first tubing segment when the pressure in said set at said Y-site is higher than the pressure in said first tubing segment, distal from said Y-site;
   said Y-site having a second branch which includes means for connecting another administration set to said Y-site;
   said Y-site having a third branch connected to one end of a second tubing segment;
   said second tubing segment being adapted for connection at its other end to a patient's blood vessel via a variable volume pump chamber;
   said second tubing segment including a fluid reservoir segment which is adapted to receive and hold a volume of fluid which is approximately greater than the fluid capacity of the variable volume pump chamber and is available to be drawn into the variable volume pump chamber when the pump chamber is being filled, said reservoir segment having flexible walls so that said reservoir segment will contract when it is being emptied and expand when it is being filled.

2. An intravenous administration set according to claim 1 in which said second tubing segment is connected to an inlet side of a variable volume pumping chamber, and further comprising a third tubing segment attached at one end to an outlet side of said variable volume pumping chamber.

3. An intravenous administration set according to claim 2 further wherein said second branch connecting means comprises a fourth tubing segment connected at one end to said second branch of said Y-site and connected at its opposite end to a drip chamber; means for connecting said fourth segment to a second source of intravenous fluid; and clamping means for interrupting fluid flow in said fourth segment.

4. An intravenous administration set according to claim 1 in which said reservoir segment comprises two sheets of flexible material bonded to each other at their edges and having an inlet and an outlet to which are attached first and second portions of said second tubing segment.

5. An intravenous administration set according to claim 1 in which said reservoir segment comprises a length of expandable diameter tubing.

6. An intravenous administration set comprising:
   means for connecting said set to a source of intravenous fluid;
   a Y-site defining a first branch, a second branch, and a third branch, said second branch including means for connecting another administration set to said Y-site;
   a first tubing segment connected at one end to said means for connecting said set to a source of intravenous fluid and at a second end to said first branch of the Y-site;
   a second tubing segment connected at one end to said third branch of the Y-site and having a second end which is adapted for connection to a patient's blood vessel via a variable volume pump diameter;
   said second tubing segment including two sheets of flexible material defining edges and bounded together at the edges to define a fluid reservoir segment in fluid communication with the second tubing segment, such that said fluid reservoir receives and holds a volume of fluid that is available to be drawn into the variable volume pump chamber when the pump chamber is being filled.

7. An intravenous administration set according to claim 6 further including a drip chamber connected between said means for connecting said set to a source of intravenous fluid and said first tubing segment.

8. An intravenous administration set according to claim 6 in which said second tubing segment is connected to an inlet side of a variable volume pumping chamber, and further comprising a third tubing segment attached at one end to an outlet side of said variable volume pumping chamber.

9. An intravenous administration set according to claim 8 further wherein said second branch connecting means comprises a fourth tubing segment connected at one end to said second branch of said Y-site and connected at its opposite end to a drip chamber; means for connecting said fourth segment to a second source of intravenous fluid; and clamping means for interrupting fluid flow in said fourth segment.

10. An intravenous administration set according to claim 6 in which said reservoir segment has a fluid capacity that is greater than the fluid capacity of the pump chamber to which said set is adapted to be attached.

11. An intravenous administration set comprising:
    means for connecting said set to a source of intravenous fluid;
    a Y-site defining a first branch, a second branch, and a third branch, said second branch including means for connecting another administration set to said Y-site;
    a first tubing segment connected at one end to said means for connecting said set to a source of intravenous fluid and at a second end to said first branch of the Y-site;
    a second tubing segment connected at one end to said third branch of the Y-site and having a second end which is adapted for connection to a patient's blood vessel via a variable volume pumping chamber;
    said second tubing segment including a length of expandable diameter tubing which defines a fluid reservoir segment, said fluid reservoir segment having a fluid capacity that is approximately greater than the fluid capacity of the pump chamber to which said set is adapted to be attached such that said fluid reservoir receives and holds a volume of fluid that is available to be drawn into the variable volume pump chamber when the pump chamber is being filled.

12. An intravenous administration set according to claim 11 further including a drip chamber connected between said means for connecting said set to a source of intravenous fluid and said first tubing segment.

13. An intravenous administration set according to claim 11 in which said second tubing segment is connected to an inlet side of a variable volume pumping chamber, and further comprising a third tubing segment attached at one end to an outlet side of said variable volume pumping chamber.

14. An intravenous administration set according to claim 13 further wherein said second branch connecting means comprises a fourth tubing segment connected at one end to said second branch of said Y-site and connected at its opposite end to a drip chamber; means for connecting said fourth segment to a second source of intravenous fluid; and clamping means for interrupting fluid flow in said fourth segment.

* * * * *